United States Patent
Kogawa et al.

(10) Patent No.: US 7,959,288 B2
(45) Date of Patent: Jun. 14, 2011

(54) OPHTHALMOLOGIC IMAGER

(75) Inventors: Taisaku Kogawa, Tokyo (JP); Yuichi Sugino, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 241 days.

(21) Appl. No.: 11/887,434

(22) PCT Filed: Mar. 31, 2006

(86) PCT No.: PCT/JP2006/306951
§ 371 (c)(1),
(2), (4) Date: Sep. 10, 2009

(87) PCT Pub. No.: WO2006/106977
PCT Pub. Date: Oct. 12, 2006

(65) Prior Publication Data
US 2009/0323023 A1    Dec. 31, 2009

(30) Foreign Application Priority Data

Mar. 31, 2005 (JP) ................. 2005-101931

(51) Int. Cl.
*A61B 3/14* (2006.01)
*A61B 3/10* (2006.01)
(52) U.S. Cl. ............... 351/206; 351/205; 351/208
(58) Field of Classification Search ........... 351/200–246
See application file for complete search history.

(56) References Cited

U.S. PATENT DOCUMENTS

| 4,436,388 | A  | * | 3/1984 | Takahashi et al. | ............ 351/206 |
| 5,278,598 | A  | * | 1/1994 | Nakamura | .................... 396/131 |
| 7,377,642 | B2 | * | 5/2008 | Ishihara et al. | ............... 351/206 |

FOREIGN PATENT DOCUMENTS

| DE | 31 16380 A1 | 2/1982 |
| JP | 03-060632 A | 3/1991 |
| JP | 9-066032 A | 3/1997 |
| JP | 10-262931 A | 10/1998 |
| JP | 2000-116602 A | 4/2000 |
| JP | 2000-262478 A | 9/2000 |
| JP | 2001-286444 A | 10/2001 |
| JP | 2002-209855 A | 7/2002 |

* cited by examiner

*Primary Examiner* — Mohammed Hasan
(74) *Attorney, Agent, or Firm* — Foley & Lardner LLP

(57) ABSTRACT

An ophthalmologic imager comprises an illuminating optical system for projecting an illuminating light beam onto an ocular fundus, a light-receiving optical system having a focusing lens and serving to guiding the light reflected from the ocular fundus to an imaging section, and a focusing target projecting optical system having a bar mirror detachably inserted in the optical path of the illuminating optical system and serving to project split focusing target light beams onto the ocular fundus through the bar mirror and the illuminating optical system. A mirror image of the bar mirror is projected onto the ocular fundus by using the illuminating light beam. The ophthalmologic imager further comprises a judging device which judges the sharpness of the contour of the mirror image or the focusing target light imagers from the output of the light-receiving section and judges the focusing state by the focusing lens from the sharpness.

6 Claims, 13 Drawing Sheets

OPHTHALMOLOGIC IMAGER

TECHNICAL FIELD

The present invention relates to an ophthalmologic photographic apparatus which is designed to project focusing target light onto an ocular fundus by using a bar-like mirror disposed detachably in an optical path of an illuminating optical system, for example.

BACKGROUND ART

An ocular fundus camera is conventionally provided with: an illuminating optical system which projects an illuminating light beam onto an ocular fundus; an observing optical system which guides light reflected on the ocular fundus to a first imaging unit; and an imaging optical system that guides the light reflected on the ocular fundus to a second imaging unit. Such an ocular fundus camera has a structure that includes a focusing target projecting optical system, which is provided with a bar-like mirror detachably inserted in an optical path of the illuminating optical system and projects focusing target lights split into two onto the ocular fundus via the bar-like mirror and the illuminating optical system (for reference, see Japanese Patent Laid-Open No. 2000-262478 and Japanese Patent Laid-Open No. H9-56032).

In the ocular fundus camera, when two focusing target images by the focusing target lights split into two are split in right and left, they can be judged as being out of focus, and when the two focusing target images are vertically aligned, they can be judged as being properly focused and a focused state.

Additionally, in the ocular fundus camera, after a device main body is aligned to an eye to be examined, by operating a focusing handle or the like to operate a focusing lens provided in a light-receiving optical system back and forth in an optical axial direction, the light-receiving optical system can be focused.

However, in such an ocular fundus camera, in the case of performing focusing operation at the central portion of the ocular fundus, focusing target light is not bounced by the pupil of the eye to be examined, but in the case of imaging a peripheral portion of the ocular fundus to perform panoramic imaging or the like, the focusing target light is bounced by the pupil and it was difficult to be used for a focusing operation. In particular, in the case of imaging a peripheral portion of a fundus of a person having a small pupil, the focusing target light is surely bounced by the pupil, so that the focusing target light cannot be used for the focusing operation.

Therefore, an object of the present invention is to provide an ocular fundus camera capable of using the focusing target light in the focusing operation regardless of an imaging position of the ocular fundus.

SUMMARY OF THE INVENTION

To achieve the above-mentioned object, an ophthalmologic photographic apparatus according to one embodiment of the present invention includes an illuminating optical system that projects an illuminating light beam onto an ocular fundus; a light-receiving optical system that has a focusing lens and guides light reflected from ocular fundus to an imaging unit; a focusing target projecting optical system that includes a bar-like mirror detachably inserted in an optical path of the illuminating optical system and projects the focusing target lights split in plural numbers onto the ocular fundus via the bar-like mirror and the illuminating optical system, in which mirror image of the bar-like mirror is projected onto the ocular fundus by the illuminating light beam.

The ophthalmologic photographic apparatus is provided with a judging device that judges the sharpness of a contour of the mirror image of the bar-like mirror or the contour of the focusing target light image from the output of the light-receiving device and judges a focusing state by the focusing lens from the sharpness.

PREFERRED EMBODIMENTS OF THE INVENTION

Figure 1:
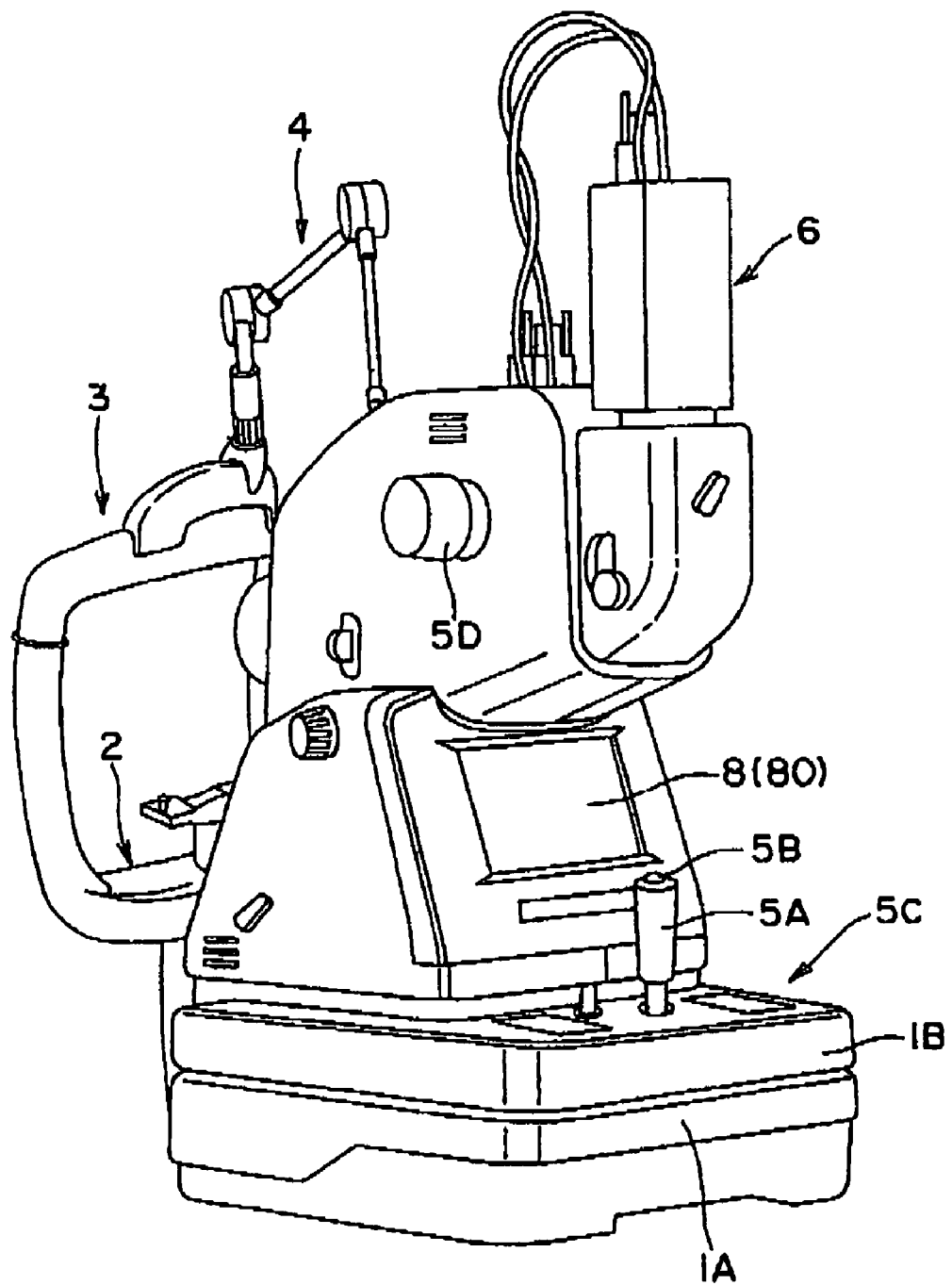
FIG. 1 is an outline view of the ophthalmologic photographic apparatus according to the present invention.

Description will be made for one embodiment of the present invention referring to the drawings below.

Examples

Structure

FIG. 1 shows the outline view of a non-mydriatic type ocular fundus camera as an example of the ophthalmologic photographic apparatus according to the present invention. In FIG. 1, reference numeral 1A denotes a base, reference numeral 1B denotes a pedestal, reference numeral 1C denotes a device main body, reference numeral 2 denotes a chin receiver, reference numeral 3 denotes a forehead receiver, reference numeral 4 denotes an external fixation lamp, reference numeral 5A denotes a joy stick, reference numeral 5B denotes an imaging switch, reference numeral 6C denotes an operation panel provided on the upper surface of the pedestal 1B, reference numeral 5D denotes a focusing handle, and reference numeral 6 denotes a television camera.

The ophthalmologic photographic apparatus is operated by the joy stick 5A, the imaging switch 5B, the various buttons or switches on the operation panel 5C or the focusing handle 5D, and additionally, can be operated based on an operation from a monitor screen 80 via a mouse (not shown) or the like. Hereinafter, these operations should be generally performed by an operation device 5.

The television camera 6 has an imaging-use television camera 6A and an observation-use television camera 6B, the imaging-use television camera 6A is connected to the monitor 8 via a still video recorder 7 as an image recording equipment, and connected to a control device (control device such as a control circuit) 9. Further, the observation-use television camera 6B is connected to the monitor 8 via the control device 9.

Figure 2:
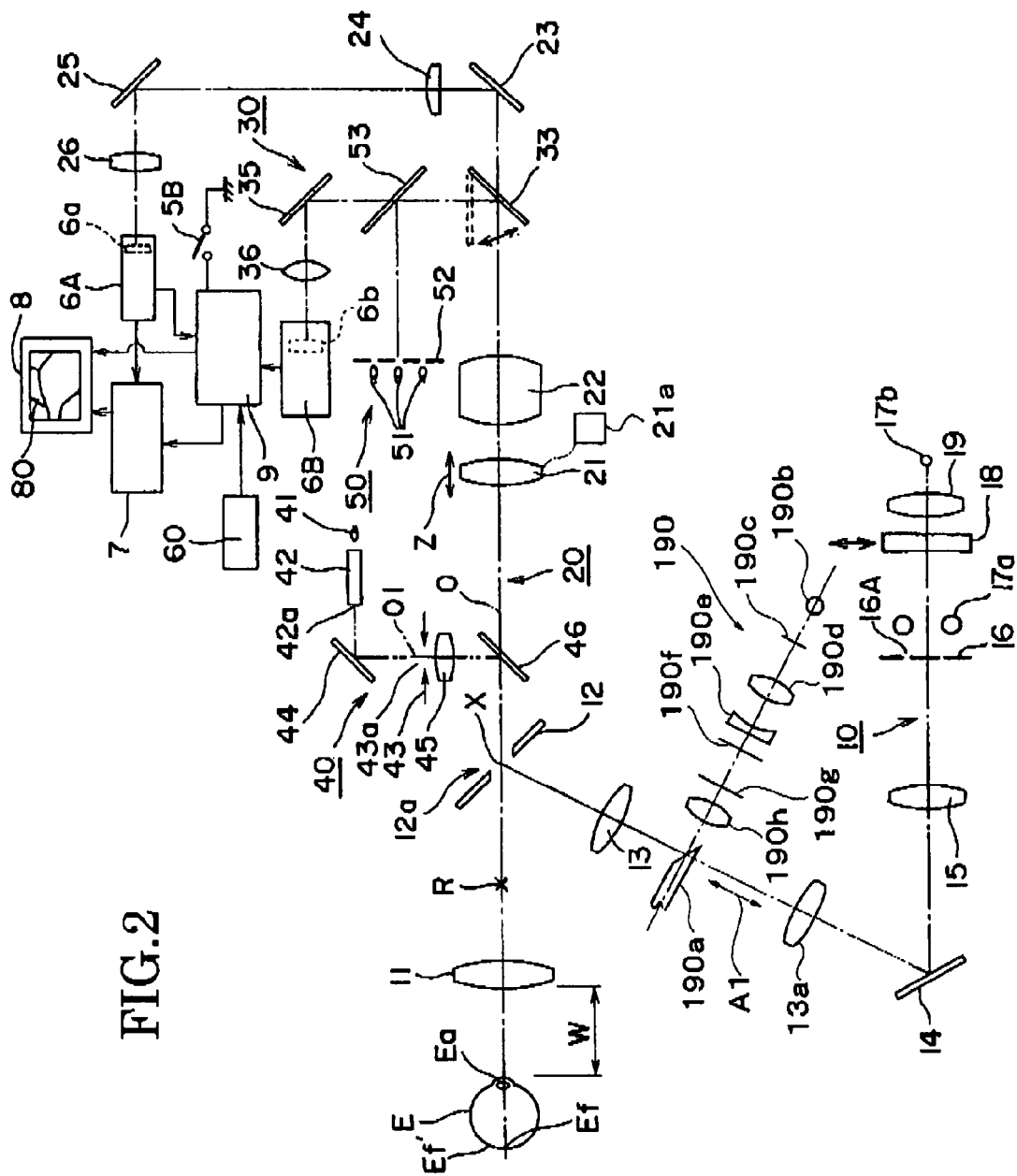
FIG. 2 is an optical diagram of the ophthalmologic photographic apparatus according to the present invention.

On the other hand, the followings are provided inside the device main body 1C: an illuminating optical system 10 for illuminating an ocular fundus Ef of eye to be examined E, for example, an imaging optical system 20 that images the ocular fundus Ef, an observing optical system 30 that observes the ocular fundus Ef, an alignment optical system 40 for performing alignment of the device main body 1C to an eye to be examined E, and an internal fixation target projecting optical system 50 that projects a fixation target onto the ocular fundus Ef and allows the eye to be examined E to fix, as shown in FIG. 2.

The illuminating optical system 10 is an optical system that illuminates the ocular fundus Ef by infrared light during observation and illuminates the ocular fundus Ef by visible light during imaging, and has an objective lens 11, a bored mirror 12, relay lenses (13, 13a), a reflective mirror 14, a relay lens 15, a ring opening plate 16 having a ring opening 16A, which is maintained in conjugate relationship with the pupil Ea of the eye to be examined E, a xenon lamp 17a as an imaging light source, an IR filter 18, a condenser lens 19, and a halogen lamp 17b as an observing illumination light source. Further, in the case where distance W between the eye to be examined E and the objective lens 11 is arranged at appropriate working distance, the bored mirror 12 is arranged at a position conjugate with the cornea C of the eye to be examined E.

In the optical path of the illuminating optical system 10, a bar-like mirror (target bar) 190a that constitutes a part of a focusing target projecting optical system 190, for example, is disposed detachably inserted in a position optically conjugate with the ocular fundus Ef of the eye to be examined E.

The focusing target projecting optical system 190 has a target projecting light source 190b, a pinhole plate 190c, a lens 190d, a prism 190e, a focusing target plate 190f, a two-hole diaphragm plate 190g and a lens 190h in this order. Then, target light from the target projecting light source 190b is projected onto the prism 190c via the pinhole plate 190c and the lens 190d, onto the reflection plane of the bar-like mirror (target bar) 190a via the focusing target plate 190f, the two-hole diaphragm plate 190g and the lens 190h, and onto the ocular fundus Ef of the eye to be examined E via the relay lens 13, the bored mirror 12 and the objective lens 11. Note that the reflection plane of the bar-like mirror (target bar) 190a and the focusing target plate 190f are conjugate with each other.

Figure 12:
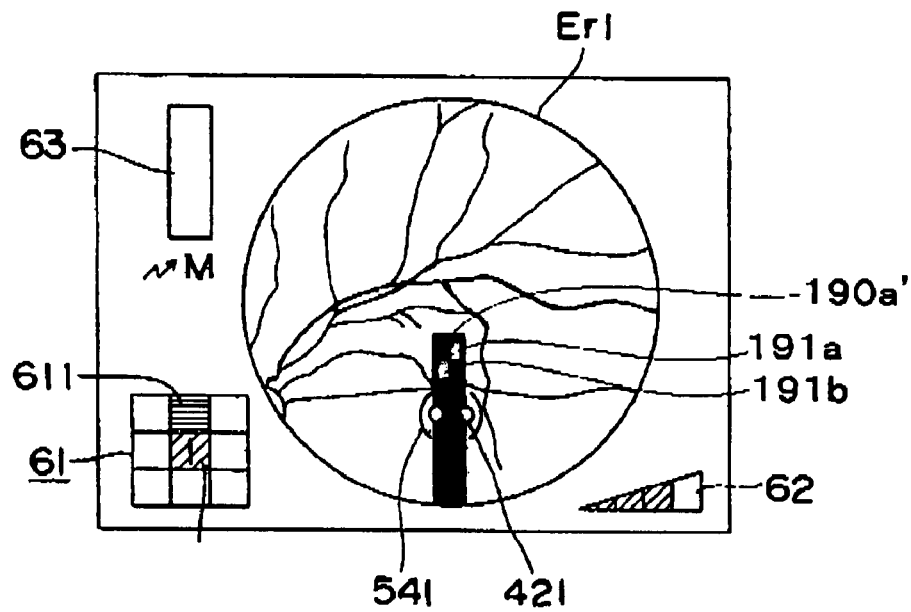
FIG. 12 is a view for describing a monitor screen for explaining the imaging procedure of an area around ocular fundus.
Figure 13:
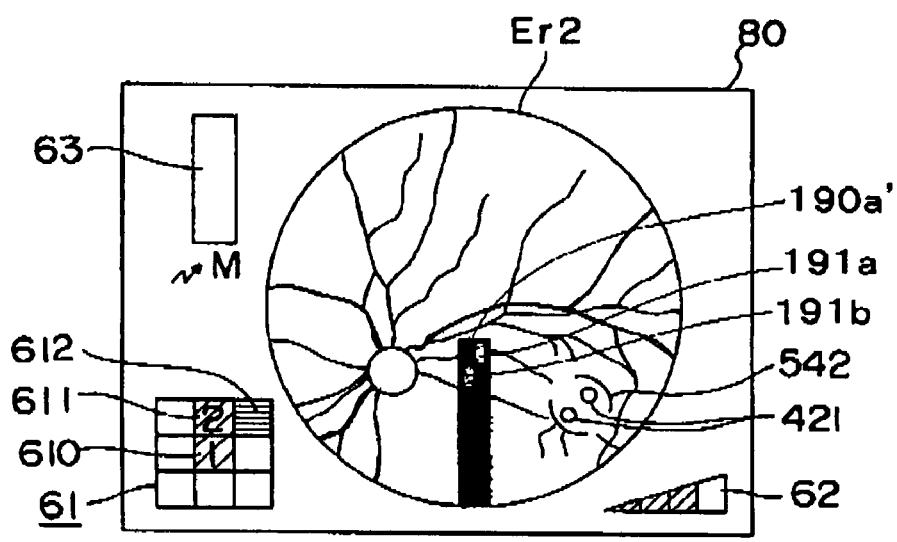
FIG. 13 is a view for describing a monitor screen for explaining the imaging procedure of an area around ocular fundus.

Additionally, focusing target light beam is split into two by the action of the prism 190e, the two-hole diaphragm plate 190g or the like, and if the ocular fundus Ef of the eye to be examined E is not conjugate with the reflection plane of the bar-like mirror (target bar) 190a, the focusing target images (191a, 191b) look split into two on right and left as shown in FIG. 12 and FIG. 13.

Figure 10:
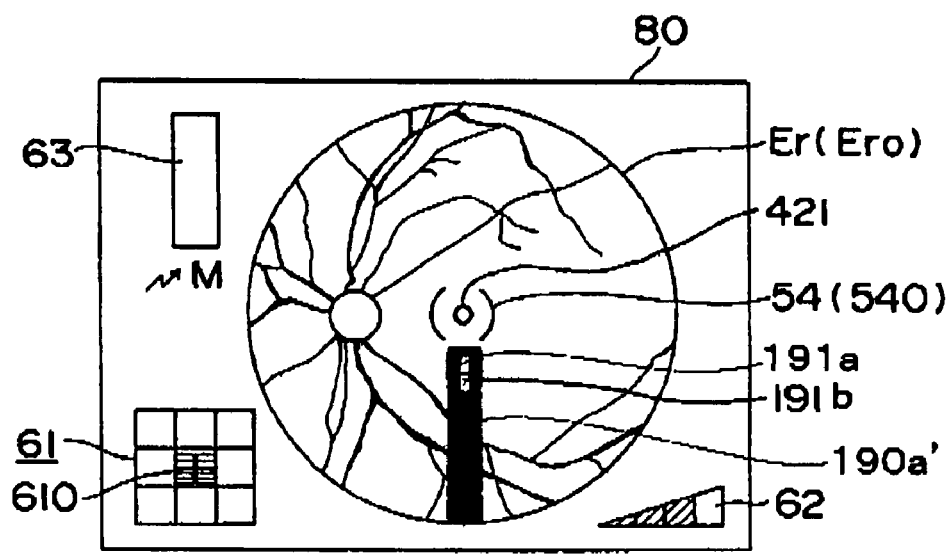
FIG. 10 is a view for describing a monitor screen for explaining the imaging procedure of a central area of an ocular fundus.

Therefore, an examiner can perform focusing simply and conveniently by making the focusing target images 191a, 191b split into two aligned in one as shown in FIG. 10.

Further, the focusing target projecting optical system 190 is designed to move in the optical axis direction of the illuminating optical system 10 as shown by an arrow A1 in conjunction with a focusing mechanism, which is a focusing lens 21 (described later) for example, provided for an observing optical system 30 and an imaging optical system 20 such that the focusing target plate 190f always becomes optically conjugate with the ocular fundus Ef.

Figure 3:
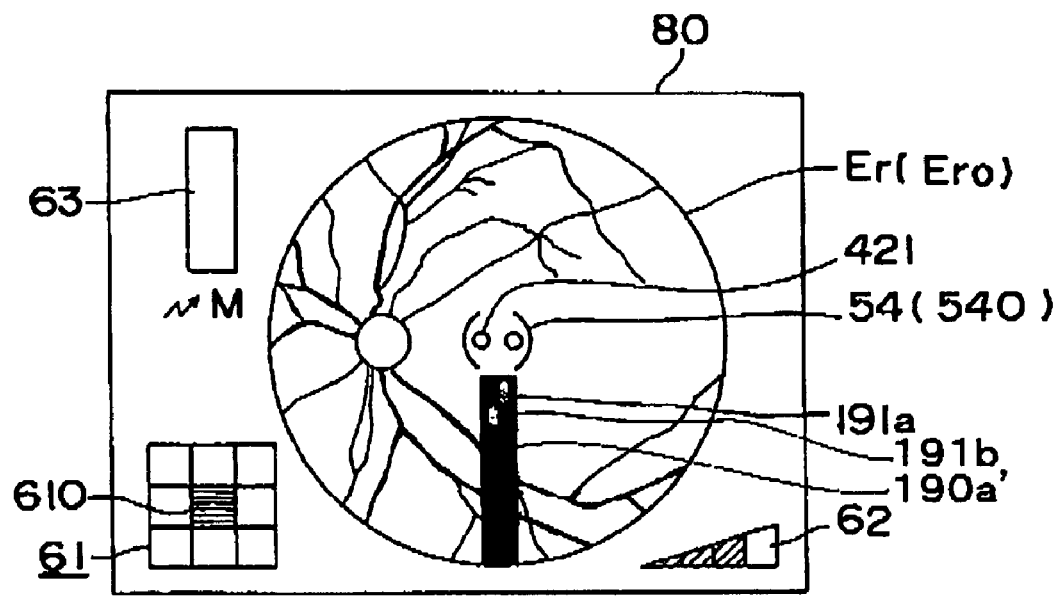
FIG. 3 is a view describing a monitor screen for describing the state where a region to be imaged is displayed on the screen in a moving image.

As described, the focusing target projecting optical system 190 is configured that the focusing target images 191a, 191b look split into two on right and left as shown in FIG. 3, FIG. 12 and FIG. 13 if the ocular fundus Ef is not conjugate with the focusing target (not shown) of the focusing target plate 190f, and the focusing target images 191a, 191b are vertically aligned into one as shown in FIG. 10 when the ocular fundus Ef becomes conjugate with the focusing target (not shown) of the focusing target plate 190f and focusing can be performed easily.

Thus, target images 191a, 191b based on the focusing target projecting optical system 190 are displayed on the monitor screen 80, and when the target images 191a, 191b are matched, it is judged that focusing has been properly done to make imaging possible. The examiner can perform focus adjustment while looking at the target images 191a, 191b.

The imaging optical system 20 is an optical system for imaging the ocular fundus Ef illuminated by the illuminating optical system as a still image, it has an objective lens 11, a bored mirror 12, a focusing lens 21, an image-forming lens 22, a reflective mirror 23, a field lens 24, a reflective mirror 25, a relay lens 26 and an imaging-use television camera 6A, and the imaging element 6a of the imaging-use television camera 6A is maintained in au optically conjugate relationship with the ocular fundus Ef.

Further, the observing optical system 30 is an optical system for observing the ocular fundus Ef illuminated by the illuminating optical system 10, it is configured by being branched from the middle of the optical path of the imaging optical system 20 by a quick return mirror 33, and has a reflective mirror 35, a relay lens 36 and an observation-use television camera 6B. The observation-use television camera 6B is arranged at a position optically conjugate with the imaging element 6a (imaging-use television camera 6A) to the quick return mirror 33.

An alignment target projecting device 40 is for projecting an alignment target toward the eye to be examined, and has an LED 41 as an alignment light source, a light guide 42 that guides the emitted light of the LED 41, a reflecting mirror 44 that reflects light outputted from the light guide 42 and guides it to a two-hole diaphragm 43, a relay lens 45, a half mirror 46 for branching from the imaging optical system 20, a bored mirror 12 and an objective lens 11.

Figure 4:
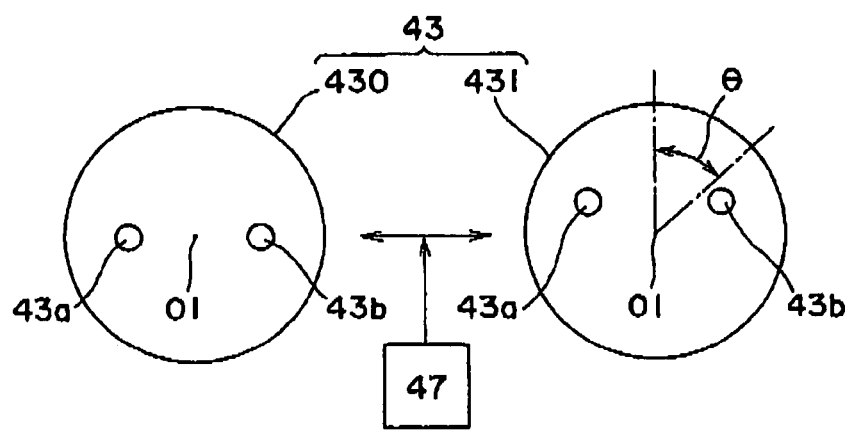
FIG. 4 is a view for describing relationship between the arrangement of the hole portions of a two-hole diaphragm shown in FIG. 2 and a switching device 47 switching the two-hole diaphragm.

The two-hole diaphragm 43 is arranged in proximity with the relay lens 45, and as shown in FIG. 4, a two-hole diaphragm 430 for nominating the central position of the ocular fundus Ef and a two-hole diaphragm 430 for nominating the peripheral position of the ocular fundus Ef are switchably inserted in the optical path by the switching operation of a two-hole diaphragm switching device 47 by a solenoid (not shown) or the like.

Each two-hole diaphragm 430 (or 431) has a pair of hole portions 43a, 43b formed on symmetrical positions regarding an optical axis O1, the hole portions 43a, 43b of the two-hole diaphragm 431 for peripheral portion are apart a little from the optical axis O1 to align the nominating position of an area around ocular fundus. Thus, separate distance between the ocular fundus Ef center portion and the peripheral area is set. Further, the two-hole diaphragm 431 for nominating the peripheral portion is designed to be rotatable in both arrow directions using the optical axis O1 as a rotation center in an inserted stated in the optical path.

The alignment target projecting device 40 is configured that, by specifying a rotation angle θ for rotating the two-hole diaphragm 431, only an angle of deviation direction is specified in the state of maintaining an equal distance from the ocular fundus Ef central area and an alignment target can be projected onto the eye to be examined E. The rotation angle θ is set to be rotated at 45-degree unit in this embodiment, but the rotation angle (set angle) θ can be freely set corresponding to a position of a fixation light source (described later).

Further, the half mirror 46 has transmission characteristic T where about half of light beam having the wavelength of 760 nm is allowed to transmit and light beam in a wavelength region other than the region is allowed to transmit substantially 100%, and reduction in the light quantity of reflected light beam from the ocular fundus Ef due to the presence of the half mirror 46 is prevented.

The LED 41 has characteristics of emitting near-infrared light having the central wavelength of 760 nm. The emission end 42a of the light guide 42 is arranged so as to be positioned on the optical axis O1 (optical axis O of imaging optical system 20) of the relay lens 45. The two-hole diaphragm 43 is an optical device for splitting an alignment image 421 based on alignment light beam and projecting it onto the eye to be examined E when working distance W is off from an appropriate position.

The alignment light beam outputted from the emission end 42a of the light guide 42 is reflected by the reflecting mirror 44 to be guided to the two-hole diaphragm 43, and the alignment light beam having passed through the hole portions 43a, 43b of the two-hole diaphragm 43 is guided to the relay lens 45. The alignment light beam having passed through the relay lens 45 is reflected by the half mirror 46 toward the bored mirror 12. The relay lens 45 temporarily forms an intermediate image of the emission end (alignment target) 42a of the light guide 42 at the central position of the hole portion 12a of the bored mirror 12 (position on the optical axis O1 of imaging optical system 20) X. A pair of alignment light beam that forms an alignment target formed at the central position X of the hole portion 12a is guided to the cornea C of the eye to be examined E via the objective lens 11.

An internal fixation target projecting optical system 50 branched by a dichroic mirror 53, which has the characteristics of transmitting infrared light from the middle of the optical path of the observing optical system 30 and reflects visible light, is arranged. The fixation target projecting optical system 50 is an optical system that projects a fixation target for guiding to the central area of the eye to be examined E (a so-called posterior pole) and its peripheral area, and has a fixation light source 51 such as a light-emitting diode, a mask plate 52 provided facing the fixation light source 51, and a dichroic mirror 53.

Figure 5:
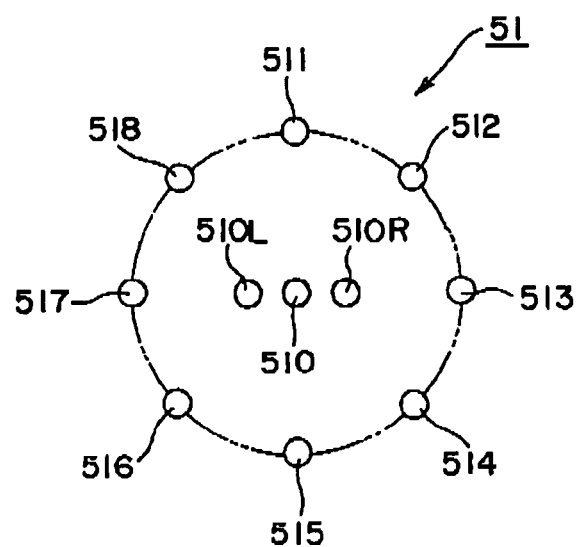
FIG. 5 is a view showing the array state of light-emitting diodes as a fixation light source shown in FIG. 2.
Figure 6:
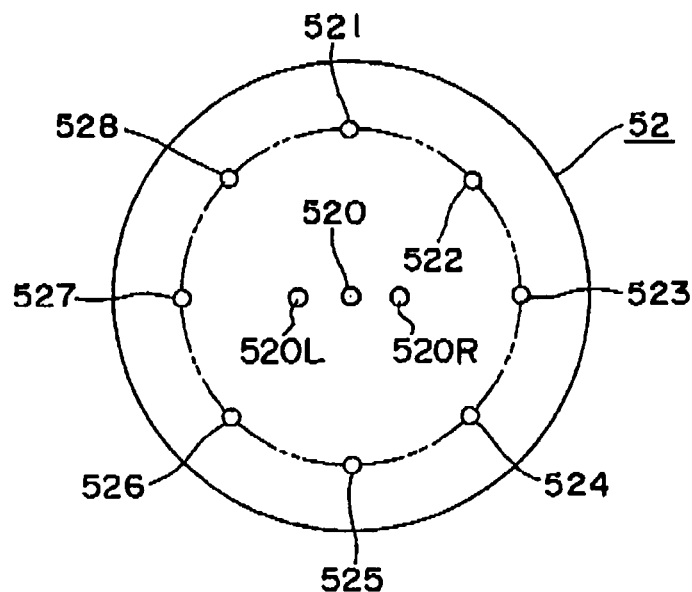
FIG. 6 is a plan view for describing the array state of the pinholes on the mask plate shown in FIG. 2.

The fixation light source 51 has a fixation light source 510 arranged at the center and eight fixation light sources 511 to 518 arranged on a circumference around the fixation light source 510 at an equal gap as shown in FIG. 5, for example. The central fixation light source 510 is for observing/imaging mainly the yellow spot area of the ocular fundus Ef, and fixation light sources 510R, 510L are for imaging a region specified by The Law of Health and Medical Services for the Aged corresponding to right and left of the eye to be examined E. Further, peripheral fixation light sources 511 to 518 are for observing/imaging the periphery of the ocular fundus Ef, and pinholes 520 (520R, 520L) to 528 are provided for the mask plate 52 facing each fixation light source 510 (510R, 510L) to 518 as shown in FIG. 6. Further, in conjunction with lighting of the fixation light source 51, the two-hole diaphragm 431 is rotated.

Light emitted from the fixation light source 51 (510 to 518) passes through each pinhole 520 to 528 of the mask plate 52, and projects pinhole images as the fixation target onto the ocular fundus Ef via the half mirror 53, the image-forming lens 22, the focusing lens 21 and the objective lens 11. Thus, the pinhole images are formed on the ocular fundus Ef and the fixation target is presented for the eye to be examined E. The fixation of an examinee is fixed by visually contacting the fixation target.

By turning any one of the fixation light sources 510 and 511 to 518 on, the fixation direction of the examinee to the optical axis O of the imaging optical system 20 is switched, and then, a region to be observed/imaged of the ocular fundus Ef can be changed. The fixation light source 51 can be set as a cross shape, a line (vertical or horizontal), a triangle, pentagon, a regular hexadecagon or the like, and the number and the arrangement of the fixation targets can be freely set.

For example, in the case where the fixation light sources 510 to 518 are sequentially turned on, in other words, in the case where the eight (octagon) fixation light sources (511 to 518) are turned on the peripheral area around the fixation light source 510, the two-hole diaphragm 431 is rotated at 45-degree unit. Further, in the case where the fixation light source 51 is turned on in a cross shape, the two-hole diaphragm 431 is rotated at 90-degree unit, and in the case where a line (fixation light sources 510, 513, 517 for example) is turned on, the two-hole diaphragm 431 is rotated at 180-degree unit.

Further, a structure is made such that alignment image reference positional mark 54 (540 to 548) is displayed on the monitor screen 80 in conjunction with lighting of the fixation light source 51 (510 to 518). Alignment reference positional marks 541 to 548 showing periphery is for previously suggesting the image-forming position of an alignment target image off from the imaging optical axis O to the examiner because cornea vertex Cf comes at a position off from the imaging optical axis O when imaging an area around ocular fundus. Thus, even when imaging the peripheral area, the examiner can easily perform alignment adjustment. Therefore, a display position of the alignment reference positional mark 54 on the monitor screen 80 is switched corresponding to the switching of the presenting position of the fixation target by a presenting position changing device (fixation target position selecting device operated by a display frame 61 (described later) or buttons 76 to 78).

The presenting position changing device (control of lighting positions of the fixation light sources 510 to 518) may be located anywhere, but in this embodiment, it depends on operation of the monitor screen 80 or operation on the operation panel during observation and during imaging.

On the monitor screen 80, a region to be imaged as a part to the entire ocular fundus Ef is displayed as the ocular fundus image Er at the center of screen as shown in FIG. 3. The ocular fundus image Er is a moving image or a still image. In FIG. 3, on the assumption that the eye to be examined E (left eye) fixedly sees the fixation light source 510L nominated by The Law of Health and Medical Services for the Aged, the monitor screen 80 displays a region to be imaged corresponding to the central portion (posterior pole) as the ocular fundus image Er O in a moving image. Meanwhile, there are cases where the fixation light source 510L and the fixation light source 510R are explained simply as the fixation light source 610 in the following description.

Further, on the monitor screen 80, a display frame (serves also as an imaging direction instructing device) 61 that displays a region being observed (or imaging region) as a part to the entire ocular fundus Ef, a brightness information frame of the illumination light source (serves also as brightness adjustment virtual slide knob) 62, an information frame 63 regarding imaging light quantity, patient information, etc., and the like are appropriately arranged on a part of the monitor screen 80, which is lower left, for example, together with the moving image displayed as the ocular fundus image Er, and these arrangements should be changeable at the initial setting of the ophthalmologic photographic apparatus or on an arbitrary step.

Figure 7:
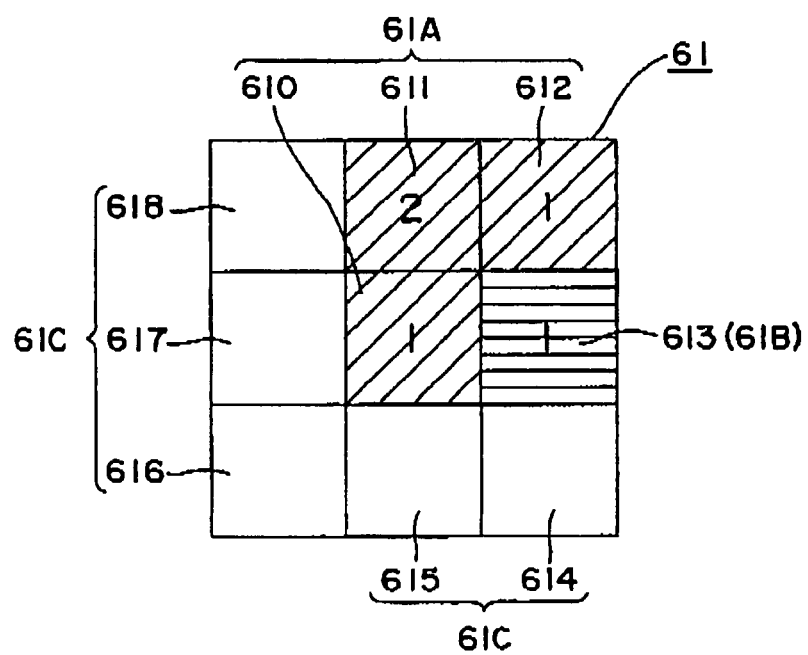
FIG. 7 is a view for describing the details of the instruction frame shown in FIG. 8.

The display frame 61 consists of nine squares 610 to 618 as shown in FIG. 7, the central square 610 corresponds to the central fixation light source 510 (or 510R, 510L), the upper (twelve o'clock direction on a clock) square 611 corresponds to the fixation light source 511, the upper right (one-thirty direction on a clock) square 612 corresponds to the fixation light source 512, and the right (three o'clock direction on a clock) square 613 corresponds to the fixation light source 513. Similarly, the square 61 . . . corresponds to the fixation light source 51 . . . , and the upper left (ten-thirty on a clock) square 618 corresponds to the fixation light source 618. The examiner, by selecting each square 610 to 618 in the display frame 61 by the operation of the mouse or the like, can select the presenting position of the fixation target, specifically, the position of a region to be imaged to the entire ocular fundus Ef. Note that a schematic view that schematically displays the pattern of the ocular fundus Ef (recognition pattern) may be drawn on the display frame 61.

Further, a proper display section, which is a dot for example, can be also used instead of the square.

It is desirable that the display frame 61 be configured that an imaged region, a region to be imaged and a region not having been imaged yet be separated by visually contacting in panoramic imaging. In the separation, brightness or chroma may be changed, the brightness or chroma of the region to be currently imaged may be relatively higher brightness or lower brightness compared to other regions, or chroma may be changed, or may be configured the region to be currently imaged is blinked so as to be visually contacted compared to other regions.

In FIG. 7, the imaged region 61A shown by a slant line area expressing a "white or outline", the region to be imaged 61B is shown by a horizontal line portion expressing a "blink", and the region not having been imaged yet 61C is separated as a no mark expressing "lower brightness or black". Further, each square (610 to 618) shows the number of still images imaged in each region by "Arabic numerals" (1, 2 . . . ).

Meanwhile, the central square 610 may be displayed in "c" in the case of the optical axis center, or "R" "L" corresponding to right and left eyes of the eye to be examined E in the case of the position nominated by The Law of Health and Medical Services for the Aged.

Thus, the imaging region that is about to be imaged is a blinking (horizontal lines) square 613 (61B), and the square 613 shows that one image has already been imaged. Further, since the squares 610, 611, 612 (61A) are white or outlined (slant lines), they show that imaging of the numbers of still images shown by number has already been completed, and squares 614 to 618 show that they are lower brightness or black (no mark) and imaging has not been done yet.

As described, by displaying the region 61B that is about to be imaged, the region not having been imaged yet 61C and the imaged region 61A on each square as a part of the entire targeted panoramic image, the examiner (imaging person) obviously understands that which area he/she is currently imaging (or observing) as a panoramic image or which region he/she should image from now on.

The operation on the display frame 61 is executable by clicking each square 610 to 618 with a mouse to turn the fixation light source 510 to 518 respectively corresponding to each square on and to fix a position to be fixedly seen (position that should be observed or imaged). Further, although the lighting position (or position that should be observed/imaged) of the fixation light source can be performed by the operation on the operation panel, its details will be described later together with the description of the operation panel.

Figure 8:
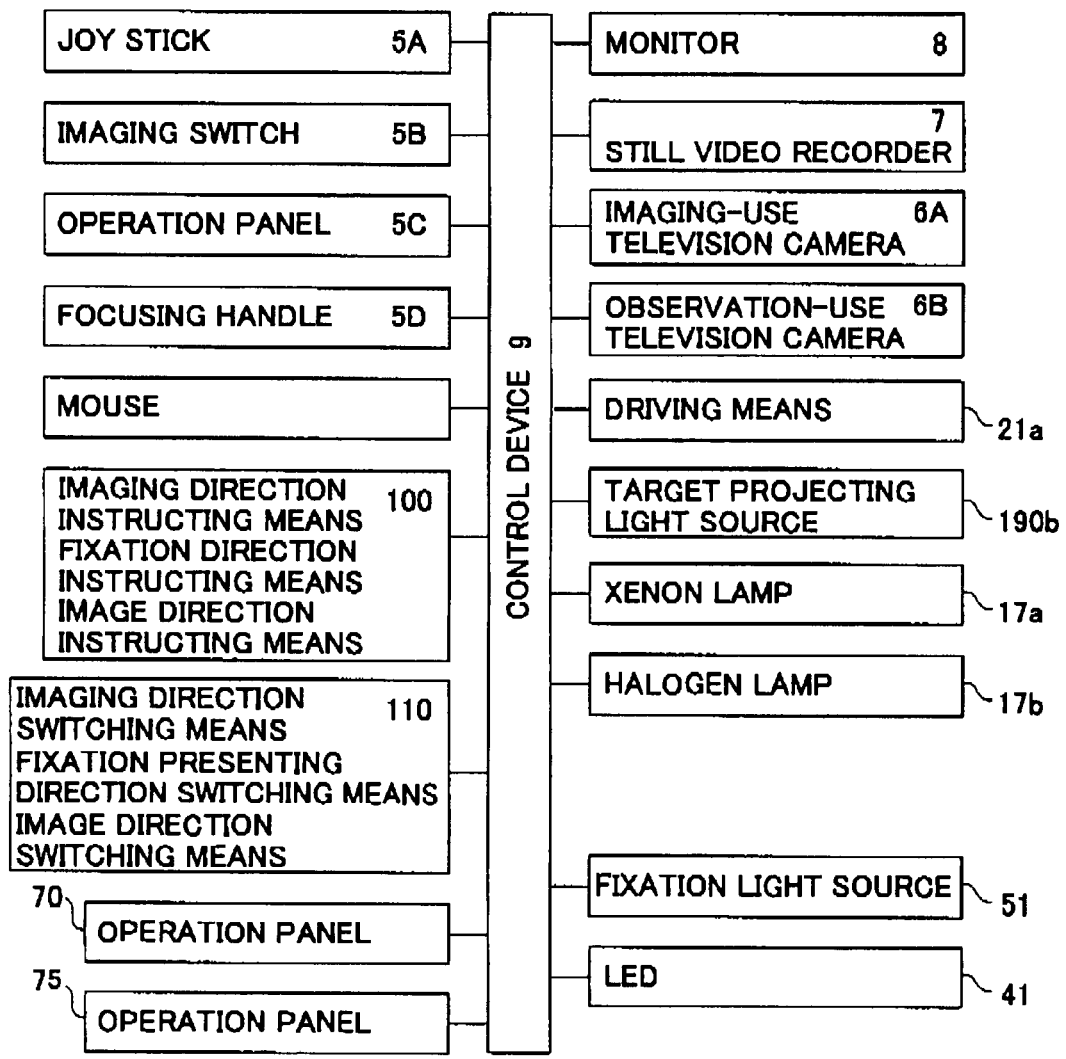
FIG. 8 is a view for describing the connection relationship to the control of the control device of the ophthalmologic photographic apparatus in FIG. 1.

Next, description will be made for connection relationship of the control device 9, referring to FIG. 8.

The control device 9 includes an arithmetic section and a storage section of a personal computer or the like, and it may be built in the ophthalmologic photographic apparatus main body or may work in conjunction with a control device such as an external personal computer. The control device 9 is connected to the monitor 8, the still video recorder 7, the imaging-use television camera 6A and the observation-use television camera 6B. In this example, the monitor 8 is built in the main body, but may be used together with the external monitor simultaneously, and the external monitor may be connected to the external personal computer (a part of the control device 9).

Further, the control device 9 is connected to various operation devices 5 and may be operated according to a previously specified program by the instruction of each operation device 5. As these operation devices 5, a joy stick 5A, an imaging switch 5B, an operation panel 5C, a focusing handle 5D, a mouse (not shown), other power sources, operation switches and the like are given, for example. Although it is connected to various alignment detection/correction circuits in xyz directions, focus detection circuits and their control circuits, drive circuits and the like, their details are omitted.

The control device or the judging device 9 controls the still video recorder 7 and the monitor 8 according to a previously set program based on various input signals from the operation devices.

For example, the ophthalmologic photographic apparatus of this invention is provided with a fixation direction instructing device as an imaging direction instructing device 100 that controls the lighting position of the fixation light source 54, and the fixation direction instructing device is controlled in conjunction with rotation control of the two-hole diaphragm 431, a selecting device of the alignment reference positional mark 54 or the like as described above. Further, in the imaging direction instructing device 100 (fixation direction instructing device), its imaging instructing direction (presenting position of fixation target) is switched such that right and left directions becomes symmetrical by the fixation target presenting direction switching device as an imaging direction switching device 110.

In the ophthalmologic photographic apparatus having a configuration including an image switching device that displays an image on the monitor screen 80 such that the right and left directions of the image are switched to become symmetrical, the imaging direction switching device 110 may be an image direction switching device that symmetrically switches the image displaying directions of the image switching device in right and left.

Such switching of imaging direction can be performed via the control device 9, and additionally, the fixation direction instructing device or the image direction instructing device may be switched by an electrical switching device such that imaging directions become symmetrical. In this embodiment, all instructing devices are conveniently connected to the control device 9 as shown in FIG. 8, and each driving device is controlled by the instruction of the control device 9.

Figure 9:
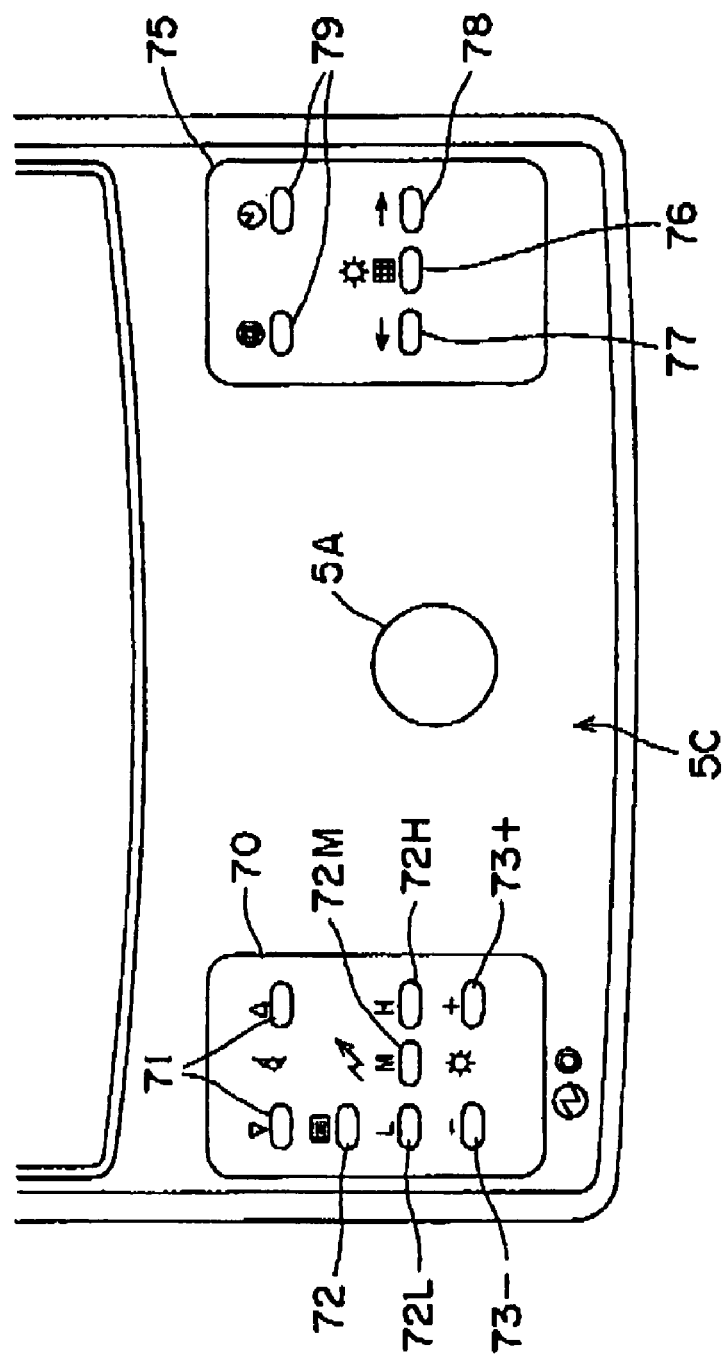
FIG. 9 is a view for describing the details of the operation panel in FIG. 1.

The operation panel 5C is configured by a left side operation panel 70 and a right side operation panel 75 around the joy stick 5A as shown in FIG. 9, and a left side operation panel 70 has a pair of button 71 down arrow and 71 up arrow (with a human mark) that moves the chin receiver 2 up and down, a menu button 72 attached with a menu mark (m mark), selection buttons (72L, 72M, 72H) attached with a lightening mark and L, M and H marks, and light quantity adjusting buttons (78+, 73−), which are attached with a sun mark, of the illumination light source.

On the other hand, three buttons for selecting a position to be imaged (which is an imaging direction instructing device and also an imaging direction switching device) are arranged at the center of the right side operation panel 75. The central button 76 is a button for returning the fixation target to the center (central portion) (equivalent to fixation target 510), a button 77 attached with a left arrow is a button for moving the presenting position of fixation target in the left direction, a button 78 attached with a right arrow is a button for moving the presenting position of fixation target in a right direction (clockwise direction). Meanwhile, with the central button 76, the fixation target may be retuned from the position 510R to 510L of The Law of Health and Medical Services for the Aged. Further, reference numeral 79 is a switch in performing fluorescence photography such as a fluorescence timer.

These operation buttons 76 to 78 may be attached with a function where the fixation target is sequentially moved by a previously programmed method in the case of panoramic imaging or the like. For example, these operation buttons 76 to 78 function as panoramic mode selection buttons, in which by pressing the button 77 or 78 after imaging at the center is finished by the button 76, it is switched to one for imaging a peripheral area, the two-hole diaphragm 431 for imaging a peripheral area is inserted, and imaging of the ocular fundus Ef at a position equivalent to the square 611 is made possible.

Next, by selecting the button 77 or 78, the presenting position of the fixation target is sequentially changed depending on whether the two-hole diaphragm 431 is rotated clockwise or rotated counter-clockwise. The alignment reference positional mark 54 is moved in conjunction with this by a position selecting device of the reference positional mark 54 and changed to be displayed at a predetermined position of the monitor screen 80, and a targeted region to be imaged can be observed and imaged as the ocular fundus images Er 1 to 8.

Thus, when imaging the pole of the ocular fundus Ef, fixation light source 510 positioned at the center is turned on, the fixation target of the pinhole 520 corresponding to it is presented on the eye to be examined E, and the central region to be imaged (ocular fundus Ef posterior pole, for example) can be imaged as an ocular fundus image ErO.

Further, when imaging the area around ocular fundus Ef, fixation light sources 511 to 518 on right, left, upper, lower or the like corresponding to an area around ocular fundus that needs to be imaged are turned on, and the fixation targets of pinholes 521 to 528 corresponding to them are presented to the eye to be examined E. Further, on the monitor screen 80, together with a moving image showing the ocular fundus Ef, the focusing target images (191a, 191b), the alignment reference positional mark 54 equivalent to a targeted position, and an alignment image 421 are displayed.

The examiner, by adjusting the target images 191a, 191b or by performing alignment adjustment such that the alignment image 421 is formed in one at the central position of the alignment reference positional mark 54, performs focusing and alignment adjustment.

When the working distance W (z direction) and the position in vertical and horizontal directions (xy direction: direction orthogonal to the optical axis O) are appropriate, the image 421 of the emission end 42a matches the center of the alignment reference positional mark 54 together with the ocular fundus image Er, and is displayed on the monitor screen 80 as shown in FIG. 10. Further, when alignment is off from an appropriate position, the image 421 of the emission end 42a is formed in a split manner as shown in FIG. 3, so the examiner can perform alignment adjustment by visually contacting the match/split of the alignment image 421 based on the alignment light beam.

[Operation]

Description will be made for an example of the observing and imaging procedure using the ocular fundus camera configured as described above.

[Initial Settings of Ocular Fundus Camera]

Prior to imaging, the examiner can perform the initial settings of the ocular fundus camera. The initial settings can be performed by operations on the monitor screen 80. For example, a menu screen is displayed by pressing the menu button 72. Similar to the initial settings of a regular ocular fundus camera, classifying necessary information and unnecessary information, a display operation such as setting a display region of the monitor screen 80, setting a reference value of imaging light quantity, and setting the selection of (selection of a signal method such as timing) an external storage device or an imaging device to be connected are done to the menu screen. Further, selection of fixation by either internal fixation or external fixation and selection of the number of internal fixations when the internal fixation is used are set in a hierarchically displayable manner.

In the case where a menu is selected, the buttons 72L, 72H are set to be changed to the operation device 5 that vertically moves the cursor on the menu screen 80. By operating the buttons 72L, 72H, the cursor is moved to a targeted position, and the menu is selected by pressing the confirm button 72M. By selecting the menu, an imaging direction switching screen is selected.

Figure 11:
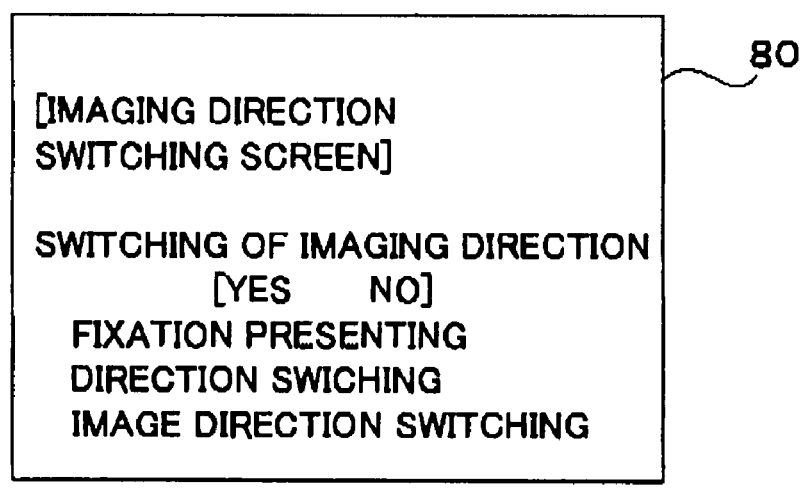
FIG. 11 is a view for describing a monitor screen for explaining the imaging procedure of an area around ocular fundus.

FIG. 11 shows an example of the monitor screen 80 displaying the imaging direction switching screen. FIG. 11 shows the state where switching of imaging direction "Yes" is selected (Yes is inverted), a "switching of fixation target presenting direction" as its selecting device is inverted and a fixation target presenting direction switching device is selected to a reverse side. By selecting or non-selecting the fixation target presenting direction switching device (switching of imaging direction), the right and left of presenting direction of fixation target are reversed. Further, by selecting the switching of imaging direction, the right and left directions of an image on the screen are reversed and displayed. The image direction switching device may not be done on the monitor screen 80. In the case of using an external personal computer, switching on the image settings screen may be performed.

[Observation of Ocular Fundus Ef and Imaging of the Central Portion of Ocular Fundus Ef]

Although the configuration is widely known and its details are omitted, a regular non-mydriatic ocular fundus camera is configured to be capable of performing a pupil image observation for observing pupil diameter Pd. Then, to observe and image an ocular fundus image Er, ocular fundus Ef observation is performed after the distance w between the ocular fundus camera and the eye to be examined E is optically adjusted to maintain appropriate distance for imaging the ocular fundus Ef.

In the case of the ocular fundus Ef observation, infrared light is illuminated on the ocular fundus Ef by the illuminating optical system 10. In the case of using the same light source, only infrared light may be selected by inserting or detaching an appropriate optical filter in the illuminating optical system 10. In this example, the halogen lamp 17b as an observing light source is turned on in the case where the IR filter 18 is inserted.

Light beam (infrared light) reflected on the ocular fundus Ef forms the image of the ocular fundus image Er on the CCD 6b of the observation-use television camera 6B by the observing optical system 30.

Then, image information of the ocular fundus, which has been imaged by the imaging section (CCD) 6b is displayed on the monitor screen 80 via the control device 9 as a black and white moving image of the ocular fundus image Er. In this occasion, the control device 9 inserts the bar-like mirror (target bar) 190a in the optical path of the illuminating optical system 10 and turns the target projecting light source 190b on. Meanwhile, the bar-like mirror (target bar) 190a is projected onto the ocular fundus Ef as a shadow by the illuminating light of the illuminating optical system 10. Then, light beam from the target projecting light source 190b is projected onto the ocular fundus Ef of the eye to be examined E as focusing target light beam via the pinhole plate 190c, the lens 190d, the prism 190e, the focusing target plate 190f, the two-hole diaphragm plate 190g, the lens 190h and via the reflection plane of the bar like mirror (target bar) 190a, the relay lens 13, the bored mirror 12 and the objective lens 11.

In such a state, the examiner operates to incline the joy stick 5A back and forth and side to side, operates to move the device main body 1 back and forth and side to side to the eye to be examined E, and observes the ocular fundus Ef while aligning the device main body 1 to the eye to be examined E looking into the monitor screen 80.

Figure 3A:
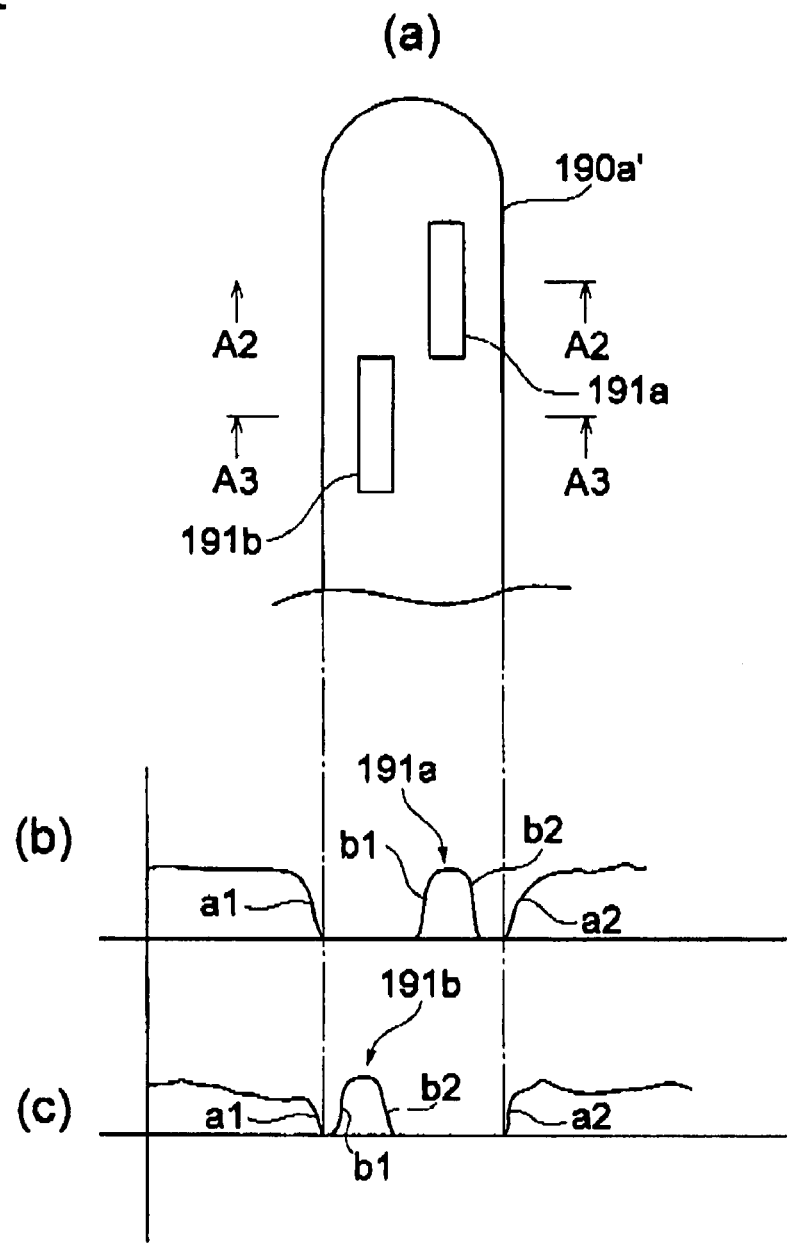
FIG. 3A (a) is an explanatory view when the bar-like mirror and focusing target image in FIG. 3 are not focused, FIG. 3A(b) is a light quantity explanatory view on the cross-section taken along line A2-A2 of FIG. 3A(a), and FIG. 3A(c) is a light quantity explanatory view on the cross-section taken along line A3-A3 of FIG. 3A(a).

Then, the control device 9, if the ocular fundus Ef of the eye to be examined E is not conjugate with the reflection plane of the bar-like mirror (target bar) 190a even when alignment to the eye to be examined E by the device main body 1 is OK, the focusing target images 191a, 191b by focusing target light beam are usually seen split into two to right and left as shown in FIG. 12 and FIG. 13. In this state, the mirror image 190a' of the bar-like mirror 190 and the periphery of the focusing target images 191a, 191b becomes a blurred state as shown in FIG. 3A(a). In other words, even if alignment becomes OK, the images usually become an out-of-focus state.

In this state, when a predetermined regional area on which the mirror image 190a' and the focusing target images (191a, 191b) to the imaging section (CCD) 6b are formed is scanned, the falling portion a1 and the falling portion a2 of the peripheral portion of the mirror image 190a' and the rising portion b1 and the falling portion b2 of the peripheral portion of the focusing target images 191a, 191b become a little drooped shape and show that they are out of focus as shown in FIG. 3A(b),(c).

Therefore, when alignment becomes OK, the control device 9 detects that the images are out of focus and a focusing direction from the split state of the two focusing target images 191a, 191b to right and left and the output of the imaging section (CCD) 6b based on the falling portion a1 and the falling portion a2, the rising portion b1 and the falling portion b2 or the like, controls the driving device 21a such as a pulse motor. Then, the driving device 21a drives the focusing lens 21 back and forth in an observation optical axis Z direction to make the ocular fundus Ef of the eye to be examined E be conjugate with the CCD 6b of the observation-use television camera 6B. In conjunction with this, the focusing target projecting optical system 190 is moved to the optical axis direction of the illuminating optical system 10, and the focusing target plate 190f is made conjugate with the ocular fundus Ef.

Figure 3B:
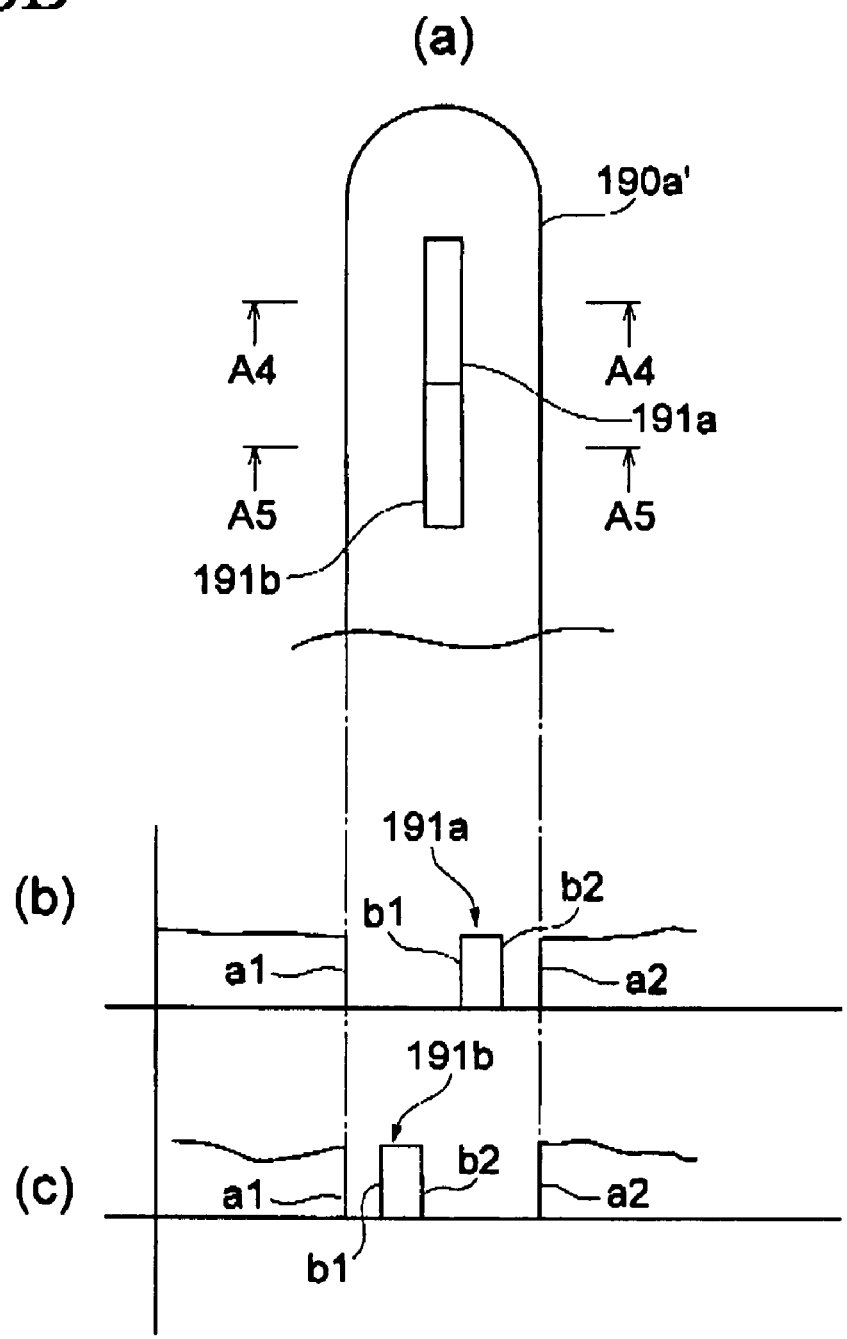
FIG. 3B (a) is an explanatory view when the bar-like mirror and focusing target image in FIG. 3 are focused, FIG. 3B(b) is a light quantity explanatory view on the cross-section along line A2-A2 of FIG. 3B(a), and FIG. 3B(c) is a light quantity explanatory view on the cross-section along line A3-A3 of FIG. 3B(a).

When the focusing target images 191a, 191b are vertically aligned into one by such focusing, the mirror image 190a' of the bar-like mirror 190 and the periphery of the focusing target images 191a, 191b becomes sharp as shown in FIG. 3B(a).

In this state, when a predetermined regional area where the mirror image 190a' and the focusing target images 191a, 191b to the CCD 6b are formed is scanned, the falling portion a1 and the falling portion a2 of the peripheral portion of the mirror image 190a' and the rising portion b1 and the falling portion b2 of the peripheral portion of the focusing target images (191a, 191b) become a perpendicular shape, and show that they are properly focused as shown in FIG. 3B(b), (c).

Therefore, when the control device 9 detects that the images are properly focused from the split state of the two focusing target images (191a, 191b) to right and left and the output of the imaging section (CCD) 6b based on the falling portion a1 and the falling portion a2, the rising portion b1 and the falling portion b2 or the like and recognizes that they are in a properly focused state, stops the movement of the focusing lens 21 in the optical axis direction by the driving device 21a.

There are cases where such a focusing state action (autofocus) does not end normally or focusing state is not satisfied after focusing. In this case, in order to allow the examiner to manually focus, the control device 9 is designed not to perform the next focusing movement after executing the above-described focusing movement once to the one time alignment.

Therefore, if autofocus does not work satisfactorily or the focusing state is not satisfied after focusing, a focusing operation can be performed manually by operating the focusing handle 5D after focusing.

Then, when focusing is completed, this state is displayed on the monitor screen 80 to notify the examiner that imaging can be performed. In the case of performing imaging according to this, when the examiner presses the imaging switch 5B, the xenon lamp 17a (visible light) being an imaging light source is allowed to emit light synchronously based on the operation of the imaging switch 5B, light reflected from the ocular fundus Ef passes through the imaging optical system 20, and the ocular fundus image Er as a color still image is image-formed on the imaging element (imaging tube) 6a of the imaging-use television camera GA.

The ocular fundus image Er image-formed on the imaging-use television camera 6A is recorded in the still video recorder 7 together with necessary image information, and a still image Er is displayed on the monitor screen 80. Herein, the necessary image information may include image information such as necessary imaging positional information for reproducing a panoramic image and information regarding a predetermined number in an imaging region other than patient name, imaged date, imaged time, imaging person's name or the like.

In observing/imaging the central portion of the ocular fundus Ef, the button 76 is selected and the square 610 is allowed to blink (horizontal lines in the figure), and thus, the fact that the central portion of the ocular fundus Ef is selected as a region being observed or to be imaged can be visually contacted (FIG. 3). In the state where imaging after completing alignment or the like is necessary, a still image ErO near the posterior pole at the center of the ocular fundus Ef is received by the imaging-use television camera by pressing the imaging switch 6B, and is displayed as the still image ErO as shown in FIG. 10. Thus, the examiner can confirm that imaging has been securely performed, and can move to the next observation/imaging. Further, the still image ErO is recorded in the still video recorder 7 after an image number (00 for example) is attached together with other image information. Further, imaged number "1" is displayed on the square 610. The moving image is displayed by pressing the imaging switch 5B again.

Further, in the above-described example, since the bar-like mirror (target bar) 190a is projected as a shadow onto the ocular fundus Ef by the illuminating light of the illuminating optical system 10, the sharpness of the periphery (of contour) of the bar-like mirror (target bar) 190a could be used for focus judgment. However, in the case where the light quantity of the illuminating light of the illuminating optical system 10 is lowered, the sharpness of the periphery (of contour) of the bar-like mirror (target bar) 190a also cannot be used for focus judgment. In this case, the sharpness of the periphery (of contour) of the focusing target images 191a, 191b is used for focus judgment.

Meanwhile, since the focusing target light is not bounced at the central portion of the ocular fundus Ef of the eye to be examined E, only misaligned/matched of the focusing target images 191a, 191b is judged and focusing movement can be executed. In other words, the control device 9 should control the driving back and forth of the focusing lens 21 in the optical axis direction by the driving device 21a so as to vertically align the focusing target images 191a, 191b. In this occasion, the sharpness of the periphery (of contour) of the bar-like mirror (target bar) 190a or the sharpness of the periphery (of contour) of the focusing target images 191a, 191b may not be used as a basis of focus judgment.

Further, even at the central portion of the ocular fundus Ef of the eye to be examined E, misaligned/matched of the focusing target images 191a, 191b is not used for judging focusing, but only the sharpness of the periphery (of contour) of the barlike mirror (target bar) 190a or the sharpness of the periphery (of contour) of the focusing target images 191a, 191b can be used as a basis of focus judgment.

As described, at the central portion of the ocular fundus Ef of the eye to be examined E, either the sharpness of the periphery (of contour) of the bar-like mirror (target bar) 190a or the sharpness of the periphery (of contour) of the focusing target images 191a, 191b, or misaligned/matched of the focusing target images 191a, 191b, or combination of them can be used as a basis of focus judgment.

Furthermore, difference between the observed image (moving image) and the imaged image (still image) is whether black and white or color, which is obvious on the monitor screen 80 but it may be approximately equal on the drawing, so that description will be made for the embodiments of the invention by attaching the same numbers to the same drawing.

[Periphery of Ocular Fundus Ef or Panoramic Imaging]

When the examiner performs the imaging of a peripheral area or selects a panoramic imaging mode at the point of finishing the imaging of the central area of the ocular fundus Ef, the control device 9 displays an ocular fundus image Er corresponding to the selection at the center of the monitor screen 80. The imaging of the peripheral area may be performed by selecting the position of the display frame 61 by a mouse or the like.

Normally, in the state where the ocular fundus image ErO at the central region is displayed on the monitor screen 80 as a moving image (state of FIG. 10), the panoramic imaging mode or the button 77 or 78 is selected. When the panoramic imaging mode or the button 77 or 78 is selected, the presenting position of fixation target is that the fixation target 511 presenting the twelve o'clock direction of the ocular fundus Ef is turned on, and the alignment reference positional mark 541 is displayed below the monitor screen 80 (six o'clock direction) as shown in FIG. 12. The square 611 is blinked in order to show that it is a position supplied for imaging, and is shown in horizontal lines in the drawing. On the other hand, the square 610 is expressed by "white" (slant lines) since it has already been imaged, and number "1" showing the imaged number is displayed on the square 610.

Incidentally, since the focusing target light is bounced in the peripheral area of the ocular fundus Ef of the eye to be examined E, focusing movement cannot be executed by the judgment based on misaligned/matched of the focusing target images 191a, 191b.

On the other hand, as described above, even if alignment becomes OK, the mirror image 190a' of the bar-like mirror 190 and periphery of the focusing target images 191a, 191b normally become a blurred state as shown in FIG. 3A(a) into an out of focus state. In this case, even if alignment becomes OK, when a predetermined regional area where the mirror image 190a' and the focusing target images 191a, 191b to the CCD 6b are formed is scanned, if the falling portion a1 and the falling portion a2 of the peripheral portion of the mirror image 190a' and the rising portion b1 and the falling portion b2 of the peripheral portion of the focusing target images 191a, 191b are in a little drooped shape as shown in FIG. 3A(b),(c), it shows that the images are out of focus.

Therefore, in the case where the panoramic imaging mode or the button 77 or 78 is selected and a peripheral area other than the square 610 is selected, the control device 9, when alignment becomes OK, detects from the output of the CCD 6b that the images are out of focus based on the falling portion a1 and the falling portion a2 and the rising portion b1 and the falling portion b2 or the like, controls the driving device 21a such as a pulse motor, drives the focusing lens 21 back and forth in the observation optical axis Z direction by the driving device 21a, and the ocular fundus Ef of the eye to be examined E is made conjugate with the CCD 6b of the observation-use television camera 6B. In conjunction with this, the focusing target projecting optical system 190 is moved to the optical axis direction of the illuminating optical system 10, and the focusing target plate 190f is made conjugate with the ocular fundus Ef.

In this state, when a predetermined regional area where the mirror image 190a' and the focusing target images 191a, 191b to the CCD 6b are formed is scanned, the falling portion a1 and the falling portion a2 of the peripheral portion of the mirror image 190a' and the rising portion b1 and the falling portion b2 of the peripheral portion of the focusing target images 191a, 191b become a perpendicular shape, which shows that the images are properly focused as shown in FIG. 3B(b),(c).

Therefore, when the control device 9 detects that the images are in a focused state based on the falling portion a1 and the falling portion a2 and the rising portion b1 and the falling portion b2 or the like from the split state of the two focusing target images 191a, 191b to right and left and the output of the CCD 6b, the device stops the movement of the focusing lens 21 in the optical axis direction by the driving device 21a.

There are cases where such a focusing state action (autofocus) does not end normally or the focusing state is not satisfied after focusing. In this case, in order to allow the examiner to manually focus, the control device 9 is designed not to perform the next focusing movement after executing the above-described focusing movement once to the one time alignment.

Therefore, if autofocus does not work satisfactorily or the focusing state is not satisfied after focusing, a focusing operation can be performed manually by operating the focusing handle 5D after focusing.

Then, when focusing is completed, this state is displayed on the monitor screen 80 to notify the examiner that imaging can be performed. Accordingly, the examiner can perform the imaging of the ocular fundus image Er1. When imaging is executed by operating the imaging switch 5B, a still image Er1 is received by the imaging-use television camera 6A via the imaging optical system 20, necessary image information is recorded in the still video recorder 7 together with image number (11, for example), and number "1" is displayed on the square 611.

At this point, although the still image Er1 is displayed on the monitor screen 80, the examiner performs imaging again because the image did not have appropriate resolution. The second imaging can be performed by clicking the square 611 by the mouse to display a moving image on the monitor screen 80, and by pressing the imaging button 5B after a necessary operation such as alignment is performed. The still image Er1 is received by the imaging-use television camera, image number is incremented by "1" to the still video recorder 7 and is recorded as "12", for example, together with necessary image information. At this point, the square 611 displays number "2" after "1" is incremented, and thus, it can be confirmed that two imagings were performed in a region corresponding to the square 611.

When the examiner operates the button 78 in order to image the next imaging region, the fixation target is rotated clockwise, and the fixation light source 512 at the upper right (one-thirty) to patient is turned on. Thus, the ocular fundus Ef in a direction of fixedly seeing upper right to the patient (ten-thirty direction to ocular fundus Ef) is displayed as a moving image Er2 at the center of the monitor screen 80 as shown in FIG. 13. At this point, the alignment position reference mark 542 is displayed at lower right of the screen (four-thirty position), the square 612 is allowed to blink (horizontal lines), and the examiner can recognize that the next imaging area is the ocular fundus image Er 2. At the same time, the square 610 and 611 becomes white (slant lines) and it is confirmed that imaging has ended.

The examiner matches the alignment image 421 with the center of the alignment reference positional mark 542 to perform alignment adjustment, and after focusing ends, executes imaging by operating the imaging switch 5B. The still image Er2 is received by the imaging-use television camera, and it is recorded in the still video recorder 7 together with image number (21 for example) and other necessary image information.

Figure 14:
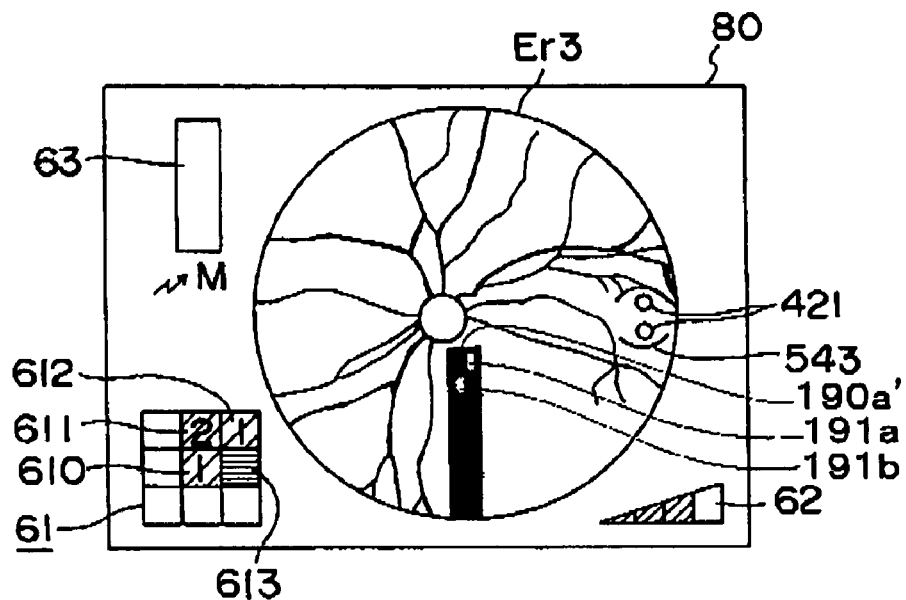
FIG. 14 is a view for describing a monitor screen for explaining the imaging procedure of an area around ocular fundus.
Figure 15:
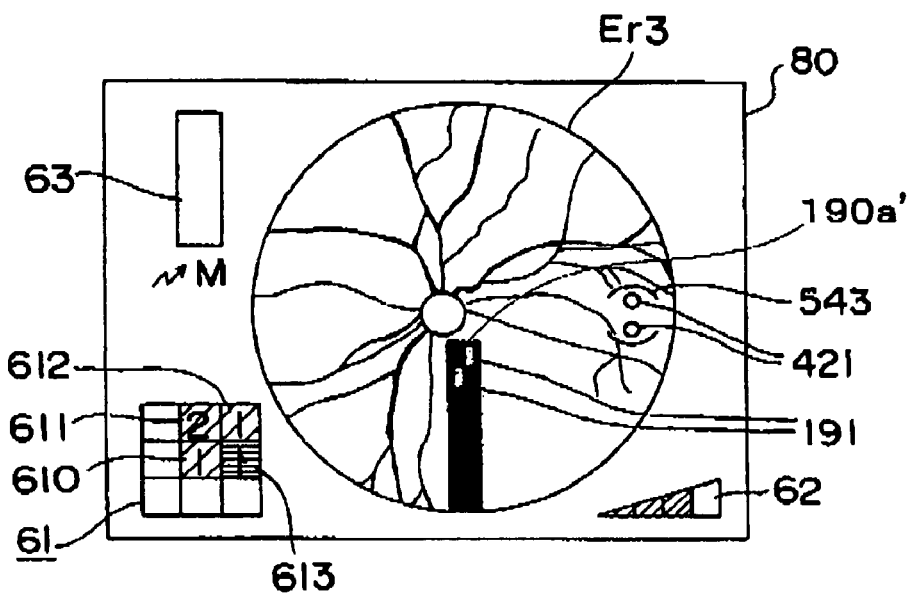
FIG. 15 is a view for describing a monitor screen for explaining the imaging procedure of an area around ocular fundus.

When the examiner clicks the square 613 for the next imaging, the fixation light source 513 is turned on, and the patient fixedly sees a fixation target displayed on the right side. Thus, the monitor screen 80 displays a moving image Er3 in a three o'clock direction (ocular fundus Ef in nine o'clock direction) to the patient as shown in FIG. 14. The examiner matches the alignment image 421 with the center of the alignment reference positional mark 543 displayed on the right side of screen (three o'clock direction) to perform alignment adjustment, and can execute imaging by operating the imaging switch 5B after focusing is finished (FIG. 15).

By repeating the above-described operations, still images corresponding to the squares from 611 to 618 are sequentially recorded in the still video recorder 7 together with necessary image information. During the recording, the examiner, while constantly visually contacting the region 61B whose imaging is being performed, the region 61C whose imaging is not performed, the region 61A whose imaging has been performed and their imaged numbers on the monitor screen 80, can perform panoramic imaging. Thus, when the examiner is observing the eye to be examined, he/she can display the imaging region 61B that is about to be imaged and its moving image Er together with the positional display of the imaging region 61A whose imaging has finished, so that when he/she is observing the imaging region 61B that is about to be imaged, can grasp instinctively its relative relationship with the imaging region 61A whose imaging has already finished.

In the case where imaging needs to be performed counterclockwise, the button 77 should be operated instead of the button 78. Further, the rotating direction of an imaging region being imaged can be done by the selection of the buttons 77, 78.

In the above operation, since the right and left directions of the examiner and the right and left directions of an image on the monitor screen 80 are reversed, in the case where an instructed imaging person such as a nurse stands in-between, it is possible that the nurse reversely operates the right and left directions by mistake when a doctor makes an instruction such as reversing an imaging direction. In such a case, since the nurse is not used to right and left reversal, such a mistake can be prevented by previously switching directions by an imaging direction switching device such that the operation direction of the button 77 and the button 78 is reversely operated based on initial settings.

Similarly, according to the ophthalmologic photographic apparatus or the monitor, which are capable of switching the right and left directions of an image on the monitor screen 80, the right and left directions of the image on the monitor screen 80 become the same as the right and left directions of the patient, so that the patient, the examiner, the nurse and the imaging instructor can execute imaging without confusion even if right or left is simply instructed based on the screen. Note that such inversion of right and left of an image can be inversed by using a widely known image processing software in the case of operating the image by an external personal computer.

Therefore, in the case where a mistake is expected to occur previously, a trouble can be prevented in advance by executing the selection of switching the presenting direction of a fixation target or switching the right and left directions of an image, by the menu screen shown in FIG. 11.

Further, by switching the right and left of the image on the monitor screen 80, all of the doctor (imaging instructor), the nurse (instructed imaging person), the patient (examinee) do not need to take the right and left directions in consideration. Specifically, in the case where the doctor (imaging instructor) wants to image left on the monitor screen 80, he/she simply instruct "left direction", and the instructed imaging person (nurse) should only perform imaging of "left direction" on the screen. Thus, the fixation target is presented in the "left direction" to the patient, and the patient can search the fixation target presented in the left direction without fail by searching the left direction according to the instruction of the doctor. As described, in the case where the imaging instructed person such as the nurse stands in between and the case where the doctor himself/herself is the imaging person, the doctor, the nurse and the patient do not need to take special consideration and do not become confused with instructing directions when the changing switch is used.

Thus, the doctor (imaging instructor or imaging person) and the nurse (imaging person or imaging instructor), even when their positions are changed, can perform imaging always in the same environment even when he/she performs imaging by an instruction on the environment that he/she has practiced, and can perform smooth imaging.

As described, by constituting the ophthalmologic photographic apparatus such that not only a specialist but also examiners in a wide range can use the imager with diversification of the imager on the position of users, it becomes possible to spread an ophthalmologic photographic apparatus capable of imaging a peripheral area of panoramic imaging.

[Formation of Panoramic Image]

Figure 16:
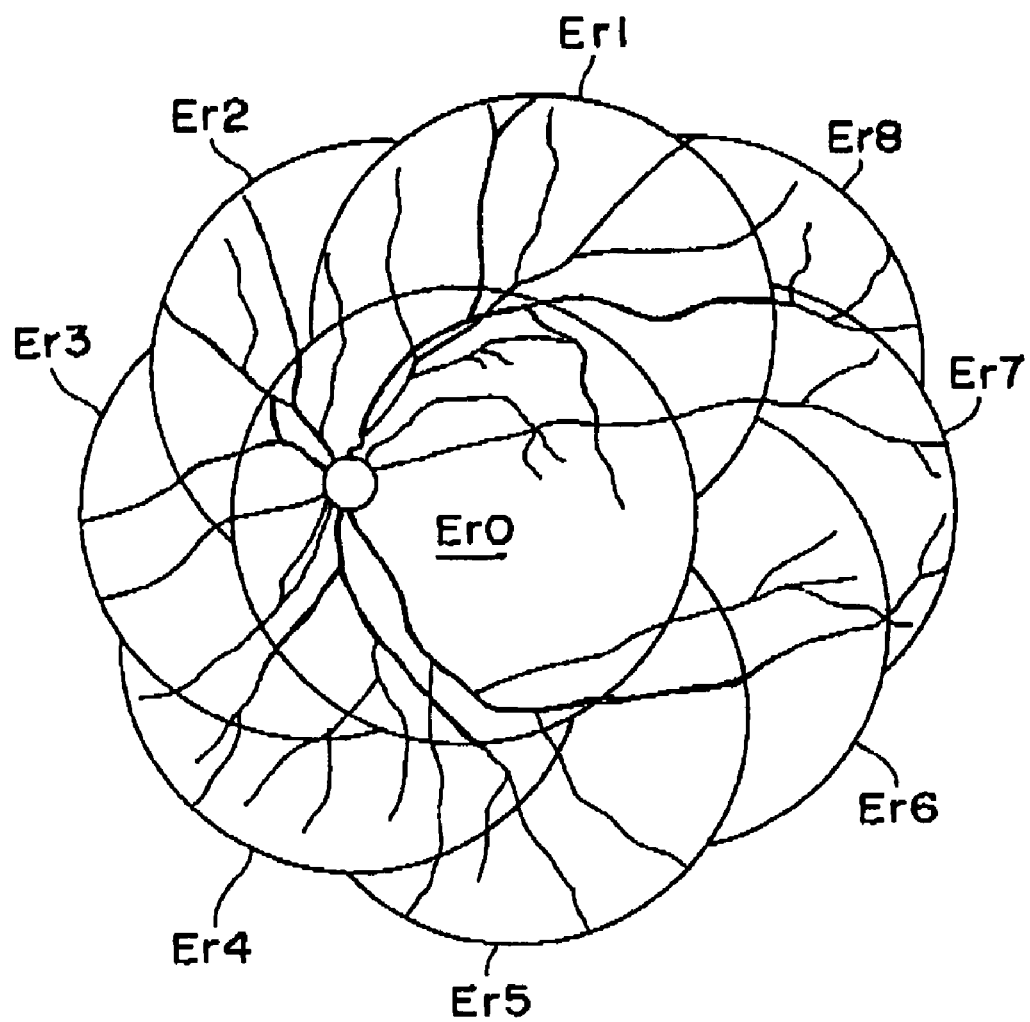
FIG. 16 is a view showing the state where several still images are connected on a monitor screen and displayed as a panoramic image.

When the formation of a panoramic image is operated by the operation device 5 after finishing the imaging of each region to be imaged (Er0 to Er8), the monitor screen 80 displays the ocular fundus image as the entire image (panoramic image) by the still images (Er0 to Er8) as shown in FIG. 16. Herein, it is assumed that there is a still image having very high brightness or a still image having very low brightness after comparing the brightness of each still image Er0 to Er8.

In such a case, the still image having high brightness or the still image having low brightness is specified by clicking an image where a cursor is positioned by moving the cursor using the operation device 5 such as a mouse. Then, the brightness adjustment virtual slide knob 62 is displayed on the monitor screen 80 simultaneously with the appearance of the specified still image on the surface of the monitor screen 80.

The brightness adjustment virtual slide knob 62 is operated on the screen by the operation device 5 to bring brightness to the one that does not have irregularity from adjacent still images, each still image can be continuously connected to compose the entire image of the eye to be examined without irregularity.

[Continuation of Imaging from Panoramic Image]

When a desired still imago (Er1 in this case) is called and specified from a panoramic image on the monitor screen 80, the still image Er1 is displayed in an enlarged manner and a display frame (or recognition pattern) 61 is displayed (refer to FIG. 10). Thus, a part of the panoramic image shown in FIG. 16 is displayed on the monitor screen 80 as the still image Er1 in an enlarged manner. When the imaging switch 5B is operated in this state, the fixation light source 511 is turned on the monitor screen 80 in order to observe the ocular fundus image Er1 in the state of maintaining a relative position with the still image Er1, and the monitor screen 80 displays the ocular fundus image Er1 shown in FIG. 10 again as a moving image. Thus, an observing region is displayed in a moving image associating with the still image on the monitor screen 80, and the control device 9 functions as a display control device controlling the images.

In this state, by operating the imaging switch 5B again after alignment adjustment, imaging of the ocular fundus imaging region Er1 can be executed again. Thus, the re-imaged still image Er1 is recorded in the still video recorder 7 together with other image information after incrementing image number by 1.

Thus, after forming the panoramic image, in the case where a part of the obtained still image Er is unclear by positional shift, out of focus comparing with another still image, imaging of an immediately necessary region can be executed while observing the panoramic image as association with the entire image is visually contacted.

As it has been described above, the ocular fundus camera of the embodiments of the invention is provided with: the illuminating optical system 10 that projects illuminating light beam onto the ocular fundus; the light-receiving optical system (imaging optical system 20, observing optical system 30) that has the focusing lens and guides light reflected from the ocular fundus to the imaging unit (CCD 6b); and the focusing target projecting optical system 190 that includes the bar-like mirror 190a detachably inserted in the optical path of the illuminating optical system and projects the focusing target light split in plural numbers onto the ocular fundus via the bar-like mirror 190a and the illuminating optical system 10. Additionally, the mirror image 190a' of the bar-like mirror is projected on the ocular fundus by the illuminating light beam. Further, the ocular fundus camera is provided with the control device 9 that judges the sharpness of the contour of the mirror image 190a' of the bar-like mirror or the contour of the focusing target light images 191a, 191b from the output of the light-receiving device (CCD 6b), and judges the focusing state by the focusing lens from the sharpness.

With this configuration, the focusing target light can be used in the focusing operation regardless of an imaging position of the ocular fundus.

INDUSTRIAL APPLICABILITY

In the above-described embodiments, although the ophthalmologic photographic apparatus according to the present invention is applied for the case of imaging the ocular fundus, it can be applied for the case of imaging a corneal endothelium or the like.

What is claimed is:

1. An ophthalmologic photographic apparatus, comprising:
an illuminating optical system which projects illuminating light beam through an objective lens onto fundus of an eye to be examined;
an imaging optical system that guides light reflected on the fundus of the eye to be examined through the objective lens and a focusing lens movable in an optical axial direction to an imaging unit;

a focusing target projecting optical system which is arranged in an optical path of said illuminating optical system, the focusing target projecting optical system including a bar-like mirror detachably arranged at a position conjugate optically with the fundus of the eye to be examined, in the optical path of the illuminating optical system and being configured to project focusing target light by the bar-like mirror through the bar-like mirror and the illuminating optical system onto the fundus of the eye to be examined, when the bar-like mirror is arranged in the optical path of said illuminating optical system such that a mirror image of the bar-like mirror and the focusing target light projected on the fundus are imaged on the imaging unit as a focusing target optical image through the imaging optical system; and a judging device configured to judge a focusing state of the focusing target optical image, wherein the judging device is configured to judge sharpness of the focusing target optical image or a contour of the mirror image of the bar-like mirror, from an output of the imaging unit and judge a focusing state by the focusing lens from the sharpness of the focusing target optical image or the contour of the mirror image.

2. The ophthalmologic photographic apparatus according to claim 1, further comprising:

an observing optical system that images the eye to be examined illuminated by the illuminating optical system as a still image.

3. The ophthalmologic photographic apparatus according to claim 2, wherein the observing optical system comprises a fixation target projecting optical system that projects a fixation target onto the central area and the peripheral area of the eye to be examined.

4. The ophthalmologic photographic apparatus according to claim 1, further comprising:

an alignment target imaging device capable of projecting an alignment target toward said eye to be examined.

5. The ophthalmologic photographic apparatus according to claim 1, further comprising:

a display device that displays a region to be imaged as a portion to the entire eye to be examined.

6. The ophthalmologic photographic apparatus according to claim 1, further comprising:

a driving device to move the focusing lens in the optical axial direction, wherein the judging device controls the driving device to perform a focusing operation of the focusing target optical image.

* * * * *